US011071651B2

United States Patent
Ingram et al.

(10) Patent No.: US 11,071,651 B2
(45) Date of Patent: Jul. 27, 2021

(54) COMBINATION HANGER ARM EXTENSION AND PUMP COVER FOR A WOUND THERAPY DEVICE

(71) Applicant: KCI LICENSING, INC., San Antonio, TX (US)

(72) Inventors: Shannon C. Ingram, Bulverde, TX (US); Benjamin A. Pratt, Poole (GB); Mauro Alanis, Helotes, TX (US); James K. Seddon, Wimborne (GB)

(73) Assignee: KCI LICENSING, INC., San Antonio, TX (US)

( * ) Notice: Subject to any disclaimer, the term of this patent is extended or adjusted under 35 U.S.C. 154(b) by 281 days.

(21) Appl. No.: 16/219,007

(22) Filed: Dec. 13, 2018

(65) Prior Publication Data
US 2019/0183684 A1 Jun. 20, 2019

Related U.S. Application Data (60) Provisional application No. 62/608,339, filed on Dec. 20, 2017.

(51) Int. Cl.
*A61F 13/00* (2006.01)
*A61M 5/00* (2006.01)
(Continued)

(52) U.S. Cl.
CPC .... *A61F 13/00068* (2013.01); *A61F 13/0216* (2013.01); *A61M 1/0058* (2013.01); *A61M 1/0088* (2013.01); *A61M 3/0258* (2013.01); *A61F 2013/00089* (2013.01); *A61M 1/0084* (2013.01); *A61M 3/022* (2014.02);
(Continued)

(58) Field of Classification Search
CPC .......... A61F 13/00068; A61F 13/0216; A61M 1/0084; A61M 1/0058; A61M 5/1407; A61M 5/1414; A61M 5/1415; A61M 5/1417
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report & Written Opinion in International Application No. PCT/US2018/065400, dated Feb. 11, 2019.
(Continued)

*Primary Examiner* — Ariana Zimbouski
(74) *Attorney, Agent, or Firm* — Foley & Lardner LLP (57) ABSTRACT

A combination hanger arm extension and pump cover device can be used with an instillation unit. The device includes a body portion that has a first end and a second end. A hook extends from the first end, and a tab extends from the body proximate the hook. A panel is disposed proximate the second end. A substantially rectangular sleeve extends at least partially through the body. The sleeve is disposed between the first and second end.

20 Claims, 7 Drawing Sheets

(51) Int. Cl.
*A61F 13/02* (2006.01)
*A61M 3/02* (2006.01)
*A61M 1/00* (2006.01)

(52) U.S. Cl.
CPC ... *A61M 3/0208* (2014.02); *A61M 2205/3344* (2013.01); *A61M 2209/082* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0228222 | A1* | 9/2010 | Williams ............ A61M 3/0208 604/500 |
| 2013/0245580 | A1* | 9/2013 | Locke ................ F04B 35/045 604/305 |

FOREIGN PATENT DOCUMENTS

| | | |
|---|---|---|
| AU | 755496 B2 | 12/2002 |
| AU | 2017201041 A1 | 3/2017 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2013/116158 A2 | 8/2013 |
| WO | WO-2014/082003 A1 | 5/2014 |

OTHER PUBLICATIONS

Kevin Ragothaman et al., "Emerging Indications For NPWT," Podiatry Today, Jun. 19, 2017 (Jun. 19, 2017 L XP055548414), (56) References Cited

OTHER PUBLICATIONS

Retrieved from the Internet: URL:https://www.podiatrytoday.com/emerging-indications-npwt.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

COMBINATION HANGER ARM EXTENSION AND PUMP COVER FOR A WOUND THERAPY DEVICE

CROSS-REFERENCE TO RELATED APPLICATIONS

This application claims the benefit of priority to U.S. Provisional Application No. 62/608,339, filed on Dec. 20, 2017, which is incorporated herein by reference in its entirety.

BACKGROUND

The present disclosure relates generally to wound therapy systems and devices, more particularly to a hanger arm extension and pump cover device for a negative pressure and instillation wound therapy device.

Negative pressure wound therapy with instillation (NPTWi) is a type of wound therapy that involves applying negative pressure (relative to atmospheric pressure) and a supply of instillation fluid to a wound site to promote wound healing. Instillation fluid may be provided to the NPTWI system from an instillation fluid container. Some NPTWi systems include a hanger arm that allows the instillation fluid container to be suspended near the NPTWi system. The configuration of the hanger arm may limit the shapes or sizes of fluid container that can be used with the system. Some NPTWi systems include a peristaltic pump which controls the flow of instillation fluid to the wound site. When an NPTWi system is not in use, the peristaltic pump may be exposed and susceptible to damage.

SUMMARY

One implementation of the present disclosure is a combination hanger arm extension and pump cover device for use with an instillation unit. The device includes a body portion that has a first end and a second end. A hook extends from the first end, and a tab extends from the body proximate the hook. A panel is disposed proximate the second end. A substantially rectangular sleeve extends at least partially through the body. The sleeve is disposed between the first and second end.

In some embodiments, the tab includes a ridge projecting toward the hook. In some embodiments, the body is formed as a single monolithic piece. In some embodiments, the body includes a pair of substantially parallel first side walls. The first side walls define a U-shaped channel there-between, and extend between the first end of the body and the sleeve.

In some embodiments, the body also includes flanges extending from a free edge of the first side walls. In some embodiments, the sleeve has an axis that extends substantially transverse to a longitudinal axis of the body, and may include a notch extending along an internal wall of the sleeve. The body may also include a wall enclosing one end of the sleeve. A slot may be formed on the wall, and the slot may have a first end substantially aligned with the notch in the sleeve.

In some embodiments, the sleeve is configured to receive a substantially rectangular hanger arm extending from the instillation unit. The slot may be configured to resiliently engage a projection extending from an end of the hanger arm. The sleeve may be configured to exert a jamming force on the hanger arm when a force is applied to the hook. The notch may be configured to substantially accommodate a projection extending from an end of the hanger arm when the sleeve receives the hanger arm. In some embodiments, the hook is configured to hold a container of instillation fluid when the sleeve receives the hanger arm.

In some embodiments, the panel includes a latching structure proximate a free end of the panel. The latching structure includes at least one substantially circular tab. The latching structure and the tab are configured to resiliently and removably engage correspondingly-shaped recesses on the instillation unit. In some embodiments, the body is configured to substantially cover a pump device on the instillation unit when the latching structure and tab are engaged with the correspondingly shaped recess.

In some embodiments, the body includes a pair of substantially parallel second side walls. The second side walls and the panel define a U-shaped opening there-between.

Another implementation of the present disclosure is a negative pressure and instillation wound therapy device. The negative pressure and instillation wound therapy device includes a housing that has a console with a user interface. A first pump is disposed within the housing, and is configured to draw a negative pressure on a wound site. A second pump is disposed within the housing. The second pump is configured to draw a supply of instillation fluid from a fluid container and deliver the instillation fluid to the wound site. Brackets are disposed on the housing adjacent to the second pump. A cassette is engageable with the brackets when the wound therapy device is in service. The cassette is configured to direct the supply of instillation fluid to the second pump. The cassette is removable from the brackets when the wound therapy device is not in service. The wound therapy device also includes an extendible and retractable hanger arm coupled to the housing. A combination hanger arm extension and pump cover is engageable with the hanger arm and can support the fluid container when the wound therapy device is in service. The combination hanger arm extension and pump cover is also engageable with the brackets to substantially cover the second pump when the wound therapy device is not in service.

In some embodiments, the combination hanger arm extension and pump cover further includes a body portion having a first end and a second end, a hook extending from the first end, a tab extending from the body proximate the hook, and a panel disposed proximate the second end. A substantially rectangular sleeve extends at least partially through the body. The sleeve is disposed between the first and second ends. In some embodiments, the sleeve is configured to receive the hanger arm.

DETAILED DESCRIPTION

Overview

Referring generally to the FIGURES, a hanger arm extension and pump cover device for use with an negative pressure wound therapy with installation unit and components thereof are shown, according to an exemplary embodiment. The hanger arm and pump cover device includes a body portion that has a first and second end, a hook that extends from the first end, a tab that extends from the body proximate the hook, a panel disposed proximate the second end, and a substantially rectangular sleeve that extends at least partially through the body. The sleeve is disposed between the first and second end.

Negative Pressure and Installation Wound Therapy System

Figure 1:
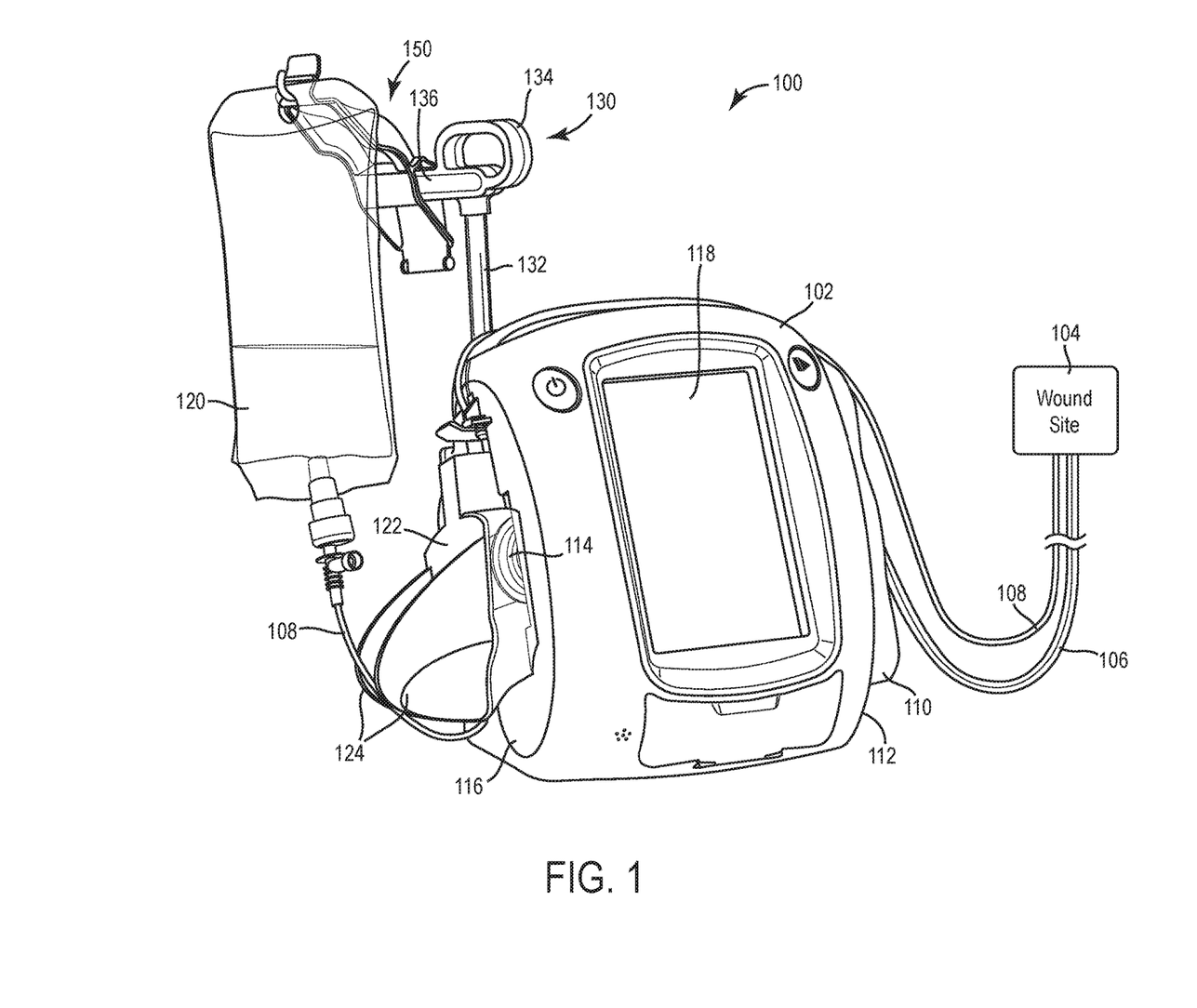
FIG. 1 is a front perspective view of a negative pressure and instillation wound therapy system including a combination hanger arm extension and pump cover device shown in an in-service condition, according to an exemplary embodiment.
Figure 2:
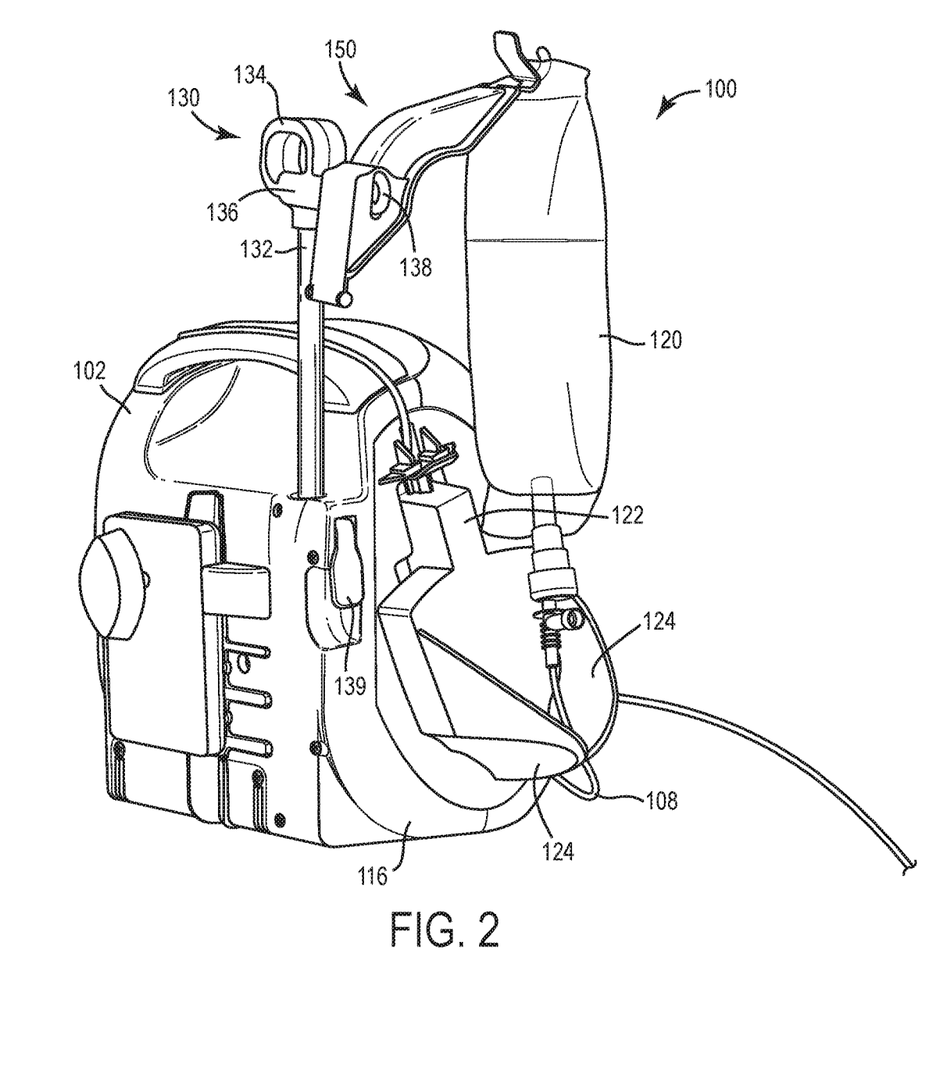
FIG. 2 is a rear perspective view of the system of FIG. 1, including the combination hanger arm extension and pump cover device and a cassette, according to an exemplary embodiment.

Referring now to FIGS. 1 and 2, a negative pressure wound therapy with installation (NPTWi) system 100 is shown in an in-service condition. NPTWi system 100 is shown to include a negative pressure and installation wound therapy unit (installation unit) 102 fluidly connected to a wound site 104 via vacuum tubing 106 and installation fluid tubing 108. Wound site 104 may include a tissue wound as well as a wound dressing that covers the tissue wound and covers the patient's skin.

Installation unit 102 can be configured to provide negative pressure wound therapy by reducing the pressure at wound site 104. Installation unit 102 can draw a vacuum or negative pressure at wound site 104 (relative to atmospheric pressure) by removing wound exudate, air, and other fluids from wound site 104 via vacuum tubing 106. Wound exudate, air, and other fluids from wound site 104 pass through the vacuum tubing 106 and are collected in canister 110 located on the left side 112 of the installation unit 102. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 104 may include installation fluid previously delivered to wound site 104.

Installation unit 102 can also be configured to provide installation fluid to the wound site 104 via installation fluid tubing 108. Installation fluid can include, for example, a cleansing fluid, a prescribed fluid, a medicated fluid, an antibiotic fluid, an irrigation fluid, or any other type of fluid which can be delivered to wound site 104 during wound treatment. Installation unit 102 may control the timing and volume of installation fluid provided to the wound site 104 using a pump, such as a peristaltic pump 114 (shown more clearly in FIG. 3), accessible from the right side 116 of the installation unit 102. Options for controlling the timing and volume of installation fluid provided to the wound site 104 may be provided on the user interface 118.

Installation fluid may originate from any installation fluid container, such as a solution bag 120 as shown. Solution bag 120 is fluidly coupled to the installation fluid tubing 108. Installation fluid may flow through the installation fluid tubing 108, which is directed into a cassette 122. The cassette 122 directs installation fluid tubing 108 to the peristaltic pump 114 (shown in FIG. 3) located along the right side 116 of installation unit 102 under the cassette 122. The installation fluid tubing 108 then runs out from the top of the cassette 122 and towards the wound site 104. The cassette 122 has side walls 124 that create a pocket configured to receive a container of installation fluid. The cassette 122 may be a single-use or limited-use consumable part, removably coupled to the installation unit 102 such that it may be removed after use. In some embodiments, the cassette 122 must be removed and/or discarded after use for sterilization or other device safety and maintenance processes.

Solution bag 120 is suspended above the cassette 122 by stand 130 and hanger arm extension and pump cover device 150. Stand 130 is shown to include a rod 132, a handle 134, a hanger arm 136, and a hook 138. The rod 132 extends vertically out of the installation unit 102. The height of the rod 132 may be adjusted by actuating release lever 139 (see FIG. 2) and sliding the rod into or out of the installation unit 102, such that the stand 130 is extendible and retractable. The installation unit 102 may be configured such that the entire length of the rod 132 can be contained within the installation unit 102 when not in use. The length of the rod 132 is limited by the height of the installation unit 102 and the resistance of the rod 132 to bending, breaking, or other deformation. The handle 134 provides an easy grip for manipulating the stand 130.

Hanger arm 136 extends at a substantially right angle from the rod 132 and provides a horizontal support for the hook 138. In some embodiments (not shown), an installation fluid container, for example solution bag 120, may be suspended directly from the hook 138. In such a configuration, the limits on the height of rod 132 discussed above may restrict the possible sizes of installation fluid container that can be properly used as part of the NPTWI system 100. As described in further detail below, some embodiments of the NPTWI system 100 include the hanger arm extension and pump cover device 150, which increases the largest possible size of solution bag 120 or other container of instillation fluid that can be used with the NPTWI system 100, among other functions (e.g., to reduce a frequency of bag replacement, etc.). The hanger arm extension and pump cover device 150 is further described in detail below with respect to FIGS. 5-8.

Figure 3:
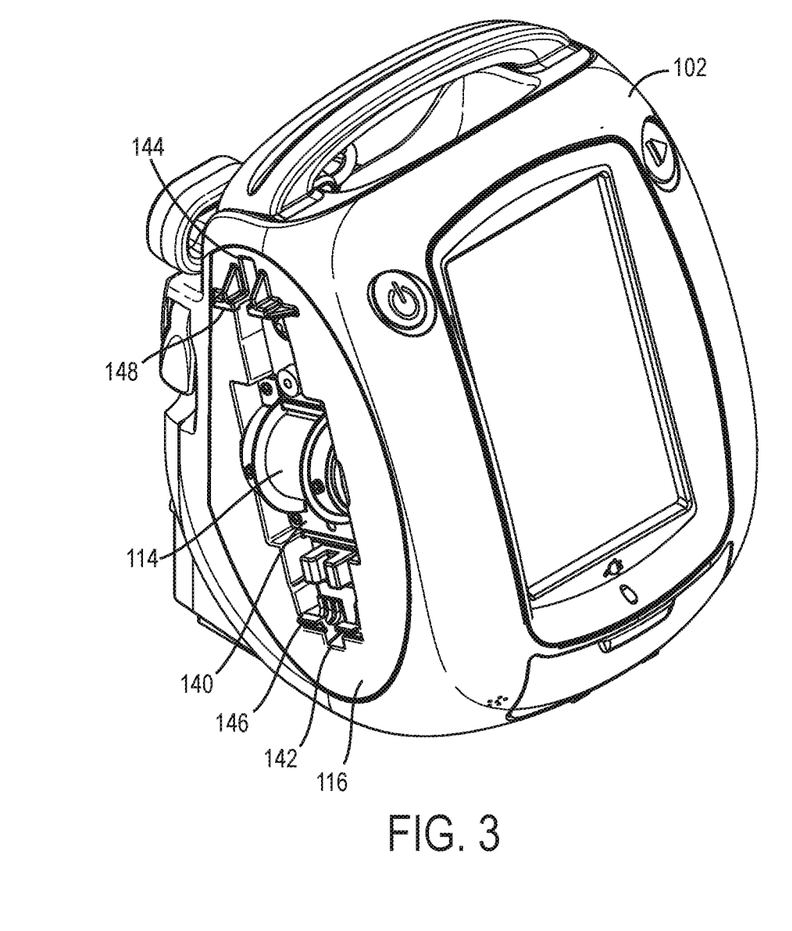
FIG. 3 is a view of the instillation unit of FIGS. 1-2 in a not-in-service condition with the cassette removed, according to an exemplary embodiment.
Figure 4:
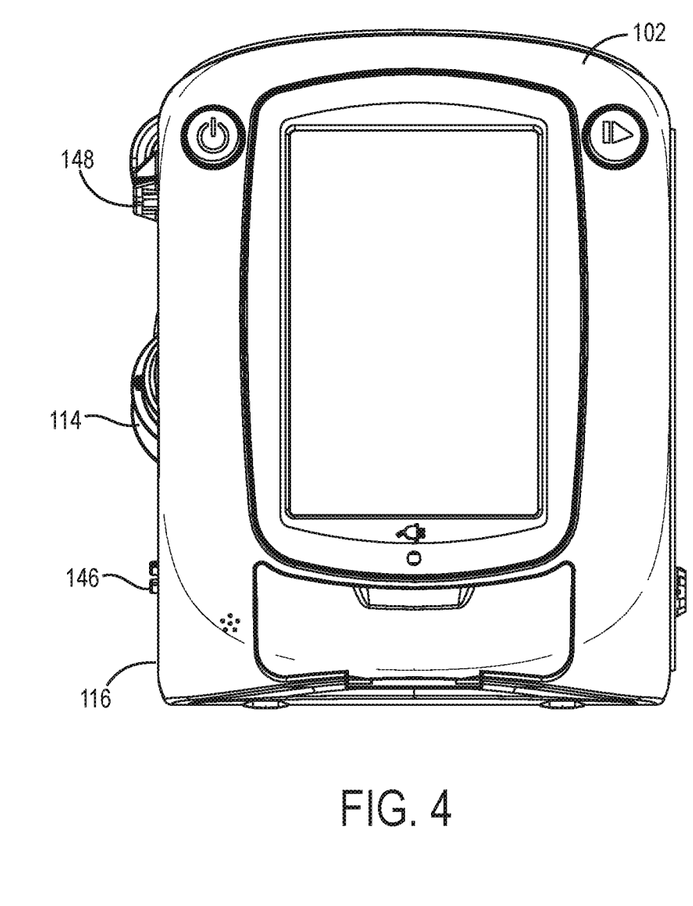
FIG. 4 is a front view of the instillation unit of FIG. 3, according to an exemplary embodiment.
Figure 7:
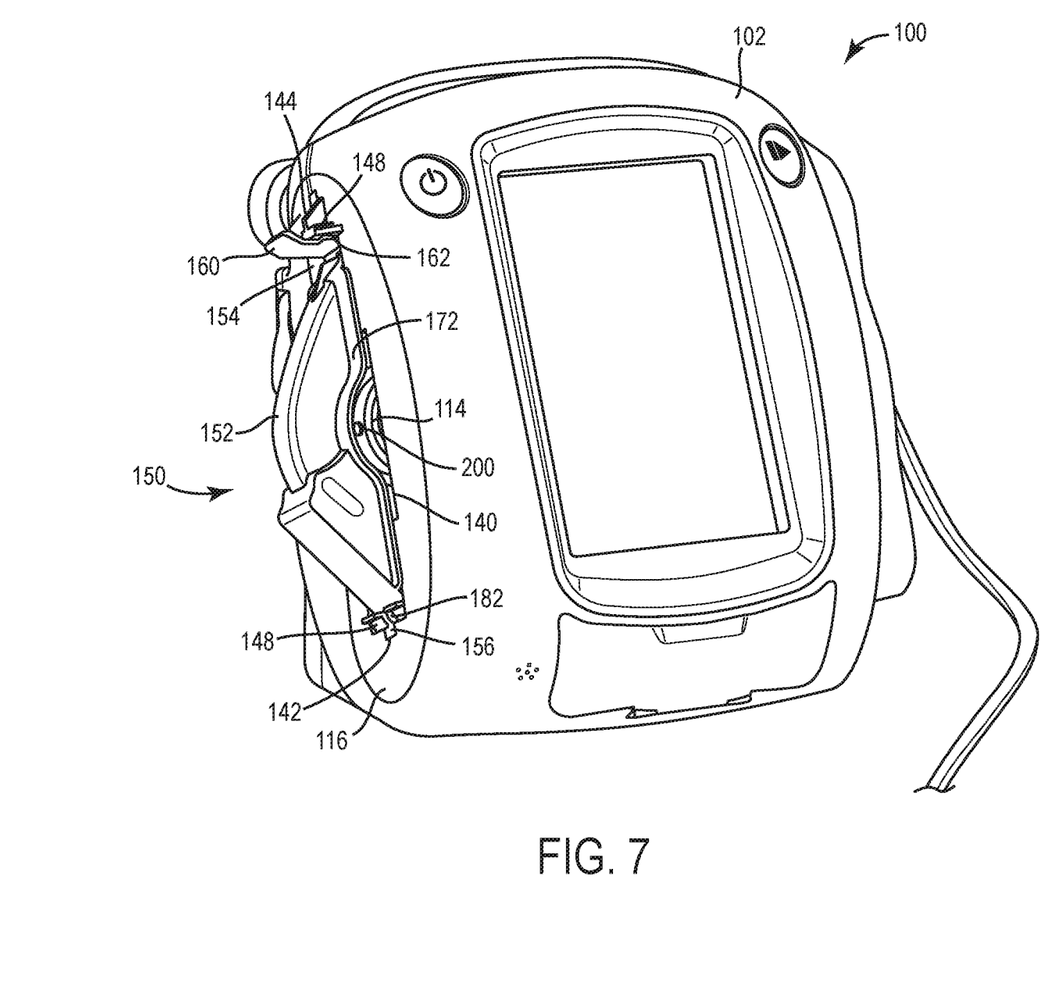
FIG. 7 is a view of the hanger arm extension and pump cover device and installation unit of FIG. 3 in a not-in-service condition, and the hanger arm extension and pump cover device in use as a pump cover, according to an exemplary embodiment.
Figures 8A, 8C:
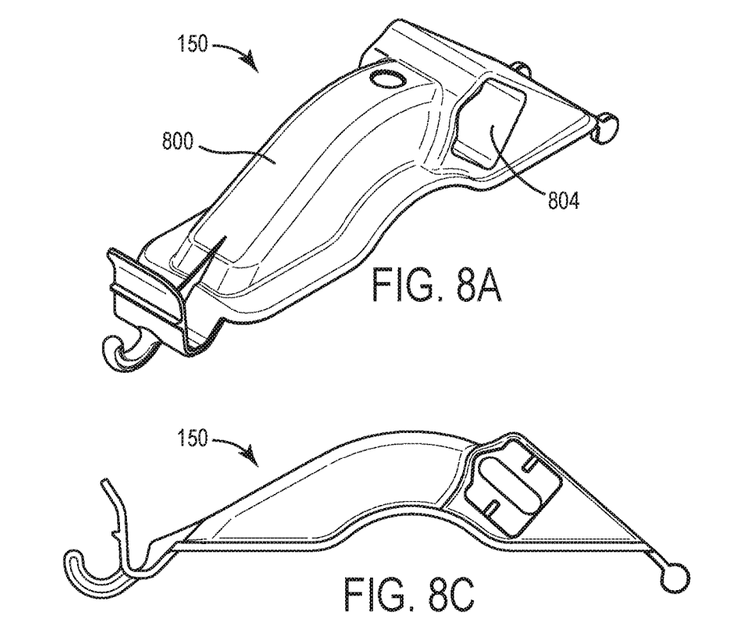
FIG. 8A is a top perspective of the hanger arm extension and pump cover device of FIGS. 1-2 and 5-7, according to an exemplary embodiment.
FIG. 8C is a right side view of the hanger arm extension and pump cover device of FIGS. 1-2 and 5-7, according to an exemplary embodiment.
Figure 8B:
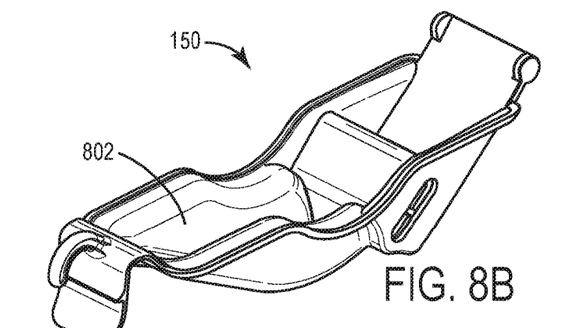
FIG. 8B is a bottom perspective of the hanger arm extension and pump cover device of FIGS. 1-2 and 5-7, according to an exemplary embodiment.
Figure 8D:
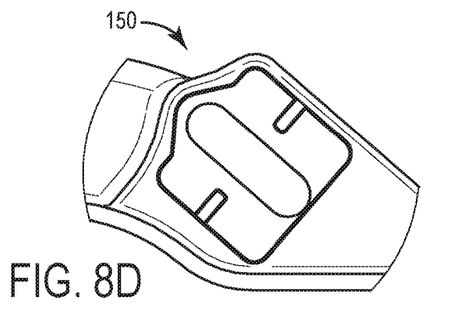
FIG. 8D is a detailed view of a portion of the hanger arm extension and pump cover device of FIG. 8C, according to an exemplary embodiment.
Figure 8E:
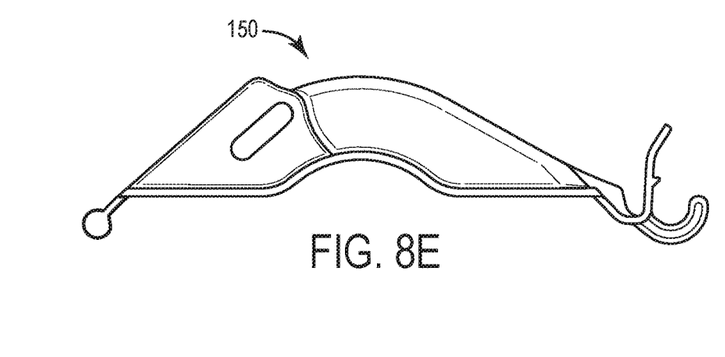
FIG. 8E is a left side view of the hanger arm extension and pump cover device of FIGS. 1-2 and 5-7, according to an exemplary embodiment.
Figure 8F:
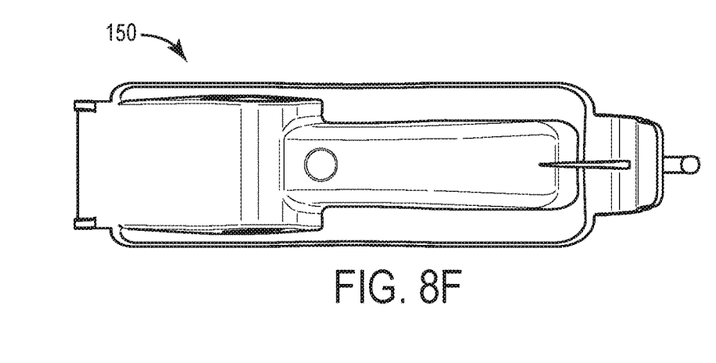
FIG. 8F is a top view of the hanger arm extension and pump cover device of FIGS. 1-2 and 5-7, according to an exemplary embodiment.

Referring now to FIGS. 3 and 4, views of the instillation unit 102 in a not-in-service condition without the cassette 122 or hanger arm extension and pump cover device 150 are shown. A recess 140 is recessed into the right side 116 of the instillation unit 102 and oriented substantially vertically along the right side 116. The recess 140 has a bottom end 142 and a top end 144. A cuff 146 is positioned within the recess 140 proximate the bottom end 142. The cuff 146 may extend out of the recess 140 and protrude from the right side 116. A clip 148 is positioned proximate the top end 144. The clip 148 may extend out of the recess 140 and protrude from the right side 116. Together, the clip 148 and the cuff 146 form brackets engageable with the cassette 122 as shown in FIGS. 1-2 and the hanger arm extension and pump cover device 150 as shown in FIG. 7.

A peristaltic pump 114 is set into the recess 140 and positioned substantially equidistant from the bottom end 142 and the top end 144. The peristaltic pump 114 may have a substantially semi-circular contour and may extend out of the recess 140 to protrude from the right side 116 of the instillation unit 102. The recess 140 may be substantially rectangular or may widen proximate the peristaltic pump 114 to accommodate the peristaltic pump 114.

Hanger Arm Extension and Pump Cover Device

Figure 5:
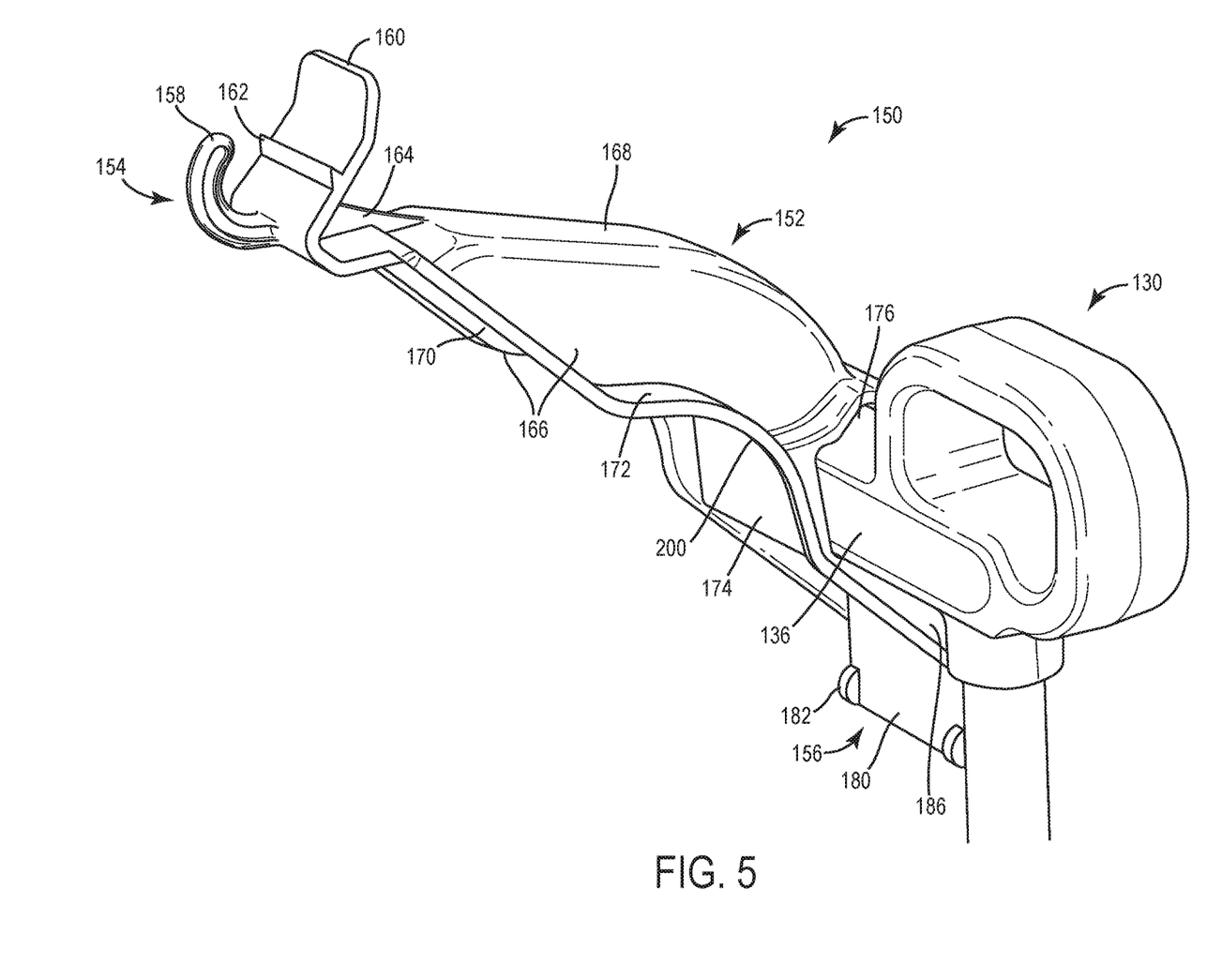
FIG. 5 is a detailed front perspective view of the hanger arm extension and pump cover device of FIGS. 1-2, in use as a hanger arm extension, according to an exemplary embodiment.
Figure 6:
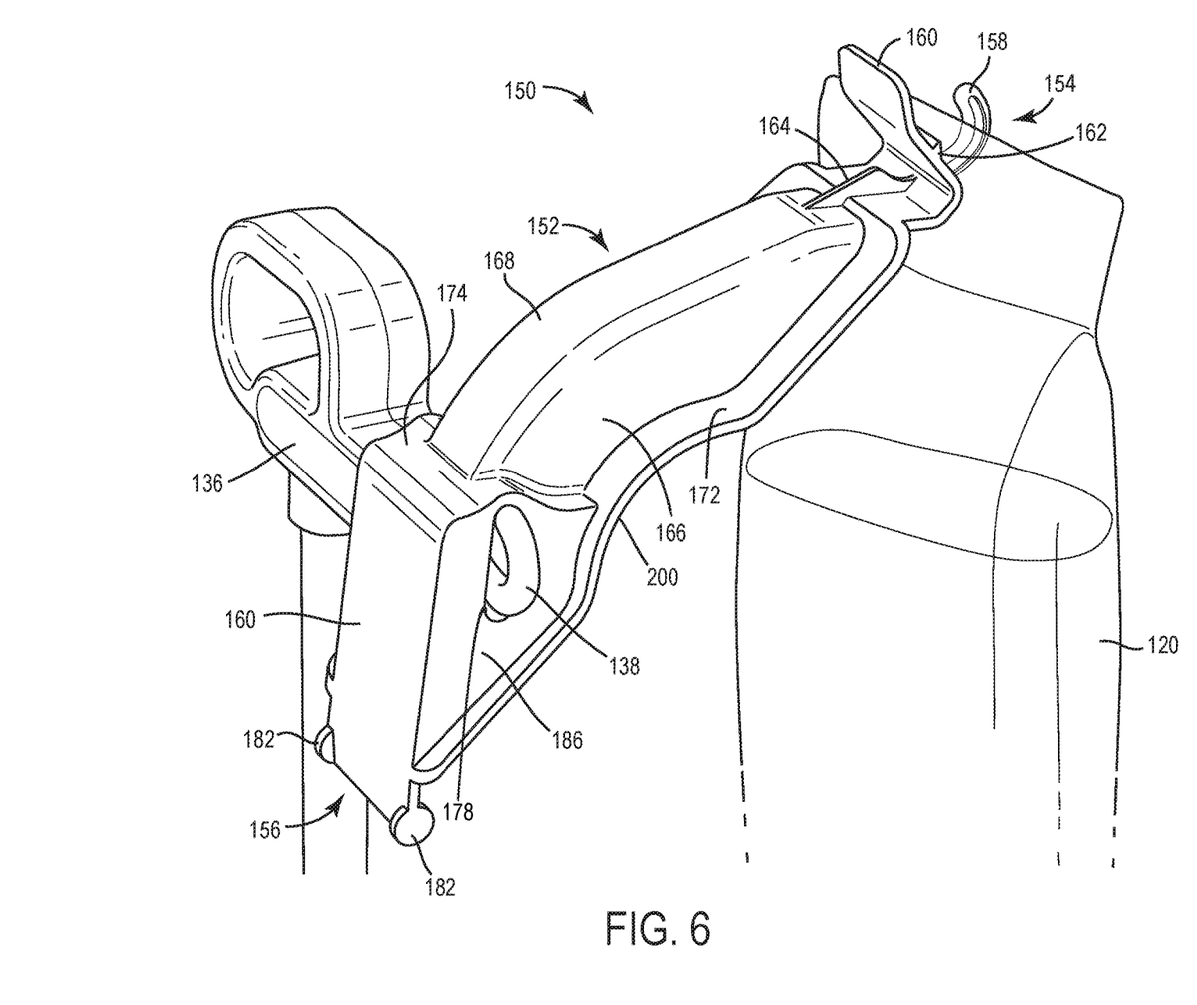
FIG. 6 is a detailed rear perspective view of the hanger arm extension and pump cover device of FIGS. 1-2, in use as a hanger arm extension, according to an exemplary embodiment.

Referring now to FIGS. 5 and 6, a first detailed view of the hanger arm extension and pump cover device 150 is shown. The device 150 has a body 152 with a first end 154 and a second end 156. A hook 158 extends at the first end 154, curving towards a tab 160. The tab 160 extends from body 152 proximate the hook 158 and is positioned between the hook 158 and the second end 156. The tab 160 is shown curving slightly away from the hook 158. A ridge 162 protrudes from the tab 160, projecting towards the hook 158. A stiffening rib 164 supports the tab 160.

The body 152 includes two first side walls 166. The first side walls 166 are substantially parallel, and are connected by a top wall 168 oriented perpendicular to the first side walls 166. The top wall 168 is aligned with the top edge of the first side walls 166. The first side walls 166 and the top wall 168 thereby combine to define a U-shaped channel 170 there-between. Flanges 172 extend from the side walls 166 along the bottom edge of the first side walls 166, that is, along the opening of the U-shaped channel 170. Flanges 172 are oriented substantially perpendicular to the first side walls 166 and are positioned outside the opening of the U-shaped channel 170.

The side walls 166 and the top wall 168 extend between the first end 154 of the body 152 and a sleeve 174. The sleeve 174 is disposed between the first end 154 and the second end 156. The sleeve 174 is shown by way of example to have a substantially rectangular shape and extends at least partially through the body 152. The sleeve 174 has an axis that runs substantially transverse to a longitudinal axis of the body 152. The sleeve 174 has a notch 176 running along an inner wall of the sleeve 174. The notch is shown as being aligned with one end of the top wall 168. A slot 178 may extend through a wall of the sleeve 174.

In some embodiments, the cross-sectional shape of the sleeve 174 is substantially the same as the cross-sectional shape of the hanger arm 136 and hook 138, but may be slightly larger to allow the device 150 to slide on and off the hanger arm 136. In some embodiments, the shape of the notch 176, slot 178, and the hook 138 contribute by ensuring that the sleeve 174 may only receive the hanger arm 136 in a single orientation. Slot 178 may be shaped substantially like the cross-section of hook 138 that extends from the hanger arm 136, and may be substantially aligned with the notch 176.

Sleeve 174 is configured to receive the hanger arm 136 of the stand 130 extending from the instillation unit 102. The notch 176 is configured to substantially accommodate passage of the hook 138 through the sleeve 174, and the slot 178 allows the hook 138 to pass out of the sleeve 174 and the body 152 when the sleeve 174 receives the hanger arm 136.

As shown in FIGS. 5 and 6, when sleeve 174 receives the hanger arm 136, the first end 154 is positioned generally above hanger arm 136. Body 152 may also be oriented such that the first end 154 and the hook 158 are separated from the hanger arm 136 in a horizontal direction.

In such a configuration, when a downward force is applied to the hook 158 which rotates the body 152 relative to the axis of the sleeve 174, the slight rotation of the sleeve 174 relative to the hanger arm 136 results in a jamming force which substantially immobilizes the device 150 relative to the hanger arm 136. The downward force, for example, may be the gravitational force caused by hanging a container of instillation fluid (for example, solution bag 120 as shown in FIG. 6) from the hook 158. In some embodiments, the slot 178 resiliently engages the hook 138 to help secure the device 150 on the hanger arm 136. As shown in FIG. 6, the hook 158 is configured to securely hold a container of instillation fluid, shown as solution bag 120, when the sleeve 174 receives the hanger arm 136.

The hanger arm extension and pump cover device 150 also includes a panel 180 disposed proximate the second end 156 of the body 152. Panel 180 may be substantially planar as shown. A pair of substantially parallel second side walls 186 extend from the panel 180 to the sleeve. The second side walls 186 and the panel 180 define a U-shaped opening 188 there-between. The panel 180 includes a latching structure, shown as circular tabs 182, positioned proximate the free end of the panel 180 (i.e., at the second end 156 of the body 152). The circular tabs 182 extend from the second end 156 of the body 152 and beyond the second side walls 186. As described in more detail below in reference to FIG. 7, the latching structure (e.g., circular tabs 182) and the tab 160 are configured to resiliently and removably engage correspondingly-shaped recesses on the instillation unit 102.

In some embodiments, flanges 172 run substantially from the first end 154 to the second end 156. Flanges 172 extend from both the second side walls 186 and the first side walls 166, along the rims of the U-shaped channel 170 and the U-shaped opening 188. Flanges 172 may be substantially planar. In some embodiments, flanges 172 include indentations 200. Indentations 200 are located between the first end 154 and the sleeve 174. Indentations 200 may be substantially semi-circular and configured to mirror the semi-circular shape of the peristaltic pump 114 shown in FIGS. 1, 3-4, and 7.

Referring now to FIG. 7, a view of the NPTWi system 100 in a not-in-service condition with the hanger arm extension and pump cover device 150 deployed as a pump cover is shown. The hanger arm extension and pump cover device 150 is positioned to substantially cover the recess 140. More particularly, the first end 154 of the body 152 is aligned with the top end 144 of the recess 140. The second end 156 of the body 152 is aligned with the bottom end 142 of the recess 140. Circular tabs 182 positioned at the second end 156 of the body 152 rotatably engage with the cuff 146. When circular tabs 182 are placed within the cuff 146, the body 152 may be rotated towards or away from the right side 116 of the instillation unit 102 around an axis defined by the circular tabs (around the second end 156 of the body 152). During the not-in-service condition, the hanger arm extension and pump cover device 150 is intended to protect the peristaltic pump 114 and to minimize ingress of contaminants.

The body 152 may then be rotated towards the right side 116 until the tab 160 and the ridge 162 engage with the clip 148. The clip 148 may be configured to receive the ridge 162 when the tab 160 is pressed towards the body 152. The tab 160 may have a resilient or springing quality such that the tab 160 can be slightly bent towards the body 152 to allow the ridge 162 to be received by the clip 148 in a "snap-fit" arrangement, and such that the tab springs back towards its original position when released to prevent the ridge 162 from leaving the clip 148. The hanger arm extension and pump cover device 150 thereby engages brackets formed by cuff 146 and clip 148. In some embodiments, the cassette 122 as shown in FIGS. 1-2 engages the brackets formed by cuff 146 and clip 148 using similar latching features.

When the cuff 146 engages the circular tabs 182 and the clip 148 engages the tab 160, the flanges 172 are positioned substantially flush against the right side 116 of the instillation unit 102 along the recess 140. Indentation 200 receives the potion of the peristaltic pump 114 that protrudes from the right side 116, such that the flanges are positioned substantially flush against the contour of the peristaltic pump 114. In this configuration, the hanger arm extension and pump cover device 150 substantially covers the recess 140 and the peristaltic pump 114. This configuration may be advantageous when the NPTWI system 100 is being used without instillation therapy (i.e., only negative pressure therapy is needed) or for shipping or storage of the NPTWI system 100. Substantially covering the recess 140 and protecting the peristaltic pump 114 helps to minimize cleaning and repairs of the NPTWI system 100.

Referring now to FIGS. 8A-F, a series of alternate views of the hanger arm and pump cover device 150 are shown. The hanger arm extension and pump cover device 150 may be formed as a single monolithic piece. The device 150 may be made from, for example, a plastic having preferred characteristics in impact resistance, chemical resistance, and stiffness, including, for example, polybutylene terephthalate. The device 150 may be injection molded, 3-D printed, or manufactured using some other suitable process. Advantageously, the device 150 may therefore be light-weight and inexpensive.

An exterior surface 800 of the body 152 may have a rough texture to facilitate handling by medical personnel. An interior surface 802 of the U-shaped channel 170 and the U-shaped opening 188 may be smooth (i.e., not textured), e.g., to avoid collection of contaminants, etc. The interior walls 804 of the sleeve 174 may also be smooth (i.e., not textured).

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

What is claimed is:

1. A combination hanger arm extension and pump cover device for use with a wound therapy with instillation unit, the device comprising:
   a body portion having a first and second end;
   a hook extending from the first end;
   a tab extending from the body proximate the hook;
   a panel disposed proximate the second end; and
   a rectangular sleeve extending at least partially through the body, the sleeve disposed between the first end and the second end.

2. The device of claim 1, wherein the tab comprises a ridge projecting toward the hook.

3. The device of claim 1, wherein the body is formed as a single monolithic piece.

4. The device of claim 1, wherein the body comprises a pair of substantially parallel first side walls, wherein the first side walls define a U-shaped channel there-between and extend between the first end of the body and the sleeve.

5. The device of claim 4, wherein the body further comprises flanges extending from a free edge of the first side walls.

6. The device of claim 1, wherein the sleeve has an axis that extends substantially transverse to a longitudinal axis of the body.

7. The device of claim 6, wherein the sleeve further comprises a notch extending along an internal wall of the sleeve.

8. The device of claim 7, wherein the body further comprises a wall enclosing one end of the sleeve, the wall having a slot formed thereon;
   wherein the slot has a first end substantially aligned with the notch in the sleeve.

9. The device of claim 7, wherein the sleeve is configured to receive a rectangular hanger arm extending from the instillation unit.

10. The device of claim 9, wherein the slot is configured to resiliently engage a projection extending from an end of the hanger arm.

11. The device of claim 9, wherein the sleeve is configured to exert a jamming force on the hanger arm when a force is applied to the hook.

12. The device of claim 9, wherein the notch is configured to substantially accommodate a projection extending from an end of the hanger arm when the sleeve receives the hanger arm.

13. The device of claim 9, wherein the hook is configured to hold a container of instillation fluid when the sleeve receives the hanger arm.

14. The device of claim 1, wherein the panel comprises a latching structure proximate a free end of the panel, the latching structure comprising at least one circular tab.

15. The device of claim 14, wherein the latching structure and the tab on the body are configured to resiliently and removably engage correspondingly-shaped recesses on the instillation unit.

16. The device of claim 15 herein the body is configured to substantially cover a pump device on the instillation unit when the latching structure and tab are engaged with the correspondingly shaped recess.

17. The device of claim 1, wherein the body comprises a pair of substantially parallel second side walls, wherein the second side walls and the panel define a U-shaped opening there-between.

18. A negative pressure wound therapy with instillation device, comprising:
- a housing having a console with a user interface;
- a first pump disposed within the housing and configured to draw a negative pressure on a wound site;
- a second pump disposed within the housing and configured to draw a supply of an instillation fluid from a fluid container and deliver the instillation fluid to the wound site;
- brackets disposed on the housing adjacent to the second pump;
- a cassette engageable with the brackets when the wound therapy device is in service, the cassette configured to direct the supply of instillation fluid to the second pump, and wherein the cassette is removable from the brackets when the wound therapy device is not in service;
- an extendible and retractable hanger arm coupled to the housing; and
- a combination hanger arm extension and pump cover engageable with the hanger arm and configured to support the fluid container when the wound therapy device is in service, and engageable with the brackets to substantially cover the second pump when the wound therapy device is not in service.

19. The wound therapy device of claim 18, wherein the combination hanger arm extension and pump cover further comprises:
- a body portion having a first and second end;
- a hook extending from the first end;
- a tab extending from the body proximate the hook;
- a panel disposed proximate the second end; and
- a rectangular sleeve extending at least partially through the body, the sleeve disposed between the first end and the second end.

20. The wound therapy device of claim 19, wherein the rectangular sleeve is configured to receive the hanger arm.

* * * * *

UNITED STATES PATENT AND TRADEMARK OFFICE
CERTIFICATE OF CORRECTION

PATENT NO. : 11,071,651 B2
APPLICATION NO. : 16/219007
DATED : July 27, 2021
INVENTOR(S) : Shannon C. Ingram

Page 1 of 1

It is certified that error appears in the above-identified patent and that said Letters Patent is hereby corrected as shown below:

In the Claims

<u>Column 9</u>
Line 1, In Claim 16, delete "claim 15 herein", and insert -- claim 15, wherein --, therefor.

Signed and Sealed this
Ninth Day of April, 2024

Katherine Kelly Vidal
*Director of the United States Patent and Trademark Office*